United States Patent
Feyh et al.

(10) Patent No.: US 9,064,800 B2
(45) Date of Patent: Jun. 23, 2015

(54) METHOD OF MANUFACTURING A SENSOR DEVICE HAVING A POROUS THIN-FILM METAL ELECTRODE

(71) Applicant: Robert Bosch GmbH, Stuttgart (DE)

(72) Inventors: Ando Feyh, Palo Alto, CA (US); Gary O'Brien, Palo Alto, CA (US); Fabian Purkl, Palo Alto, CA (US); Gary Yama, Mountain View, CA (US); Ashwin K. Samarao, Mountain View, CA (US)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 14/132,035

(22) Filed: Dec. 18, 2013

(65) Prior Publication Data

US 2014/0175523 A1    Jun. 26, 2014

Related U.S. Application Data

(60) Provisional application No. 61/745,573, filed on Dec. 22, 2012.

(51) Int. Cl.
*H01L 21/28* (2006.01)
*G01N 27/414* (2006.01)
*H01L 29/423* (2006.01)

(52) U.S. Cl.
CPC ...... *H01L 21/28008* (2013.01); *H01L 29/4238* (2013.01); *G01N 27/4146* (2013.01)

(58) Field of Classification Search
USPC ........................................................ 257/253
See application file for complete search history.

(56) References Cited

U.S. PATENT DOCUMENTS

| | | | |
|---|---|---|---|
| 2007/0049047 A1* | 3/2007 | Fujimoto et al. | 438/759 |
| 2008/0221806 A1 | 9/2008 | Bryant et al. | |
| 2010/0068623 A1* | 3/2010 | Braun et al. | 429/219 |
| 2011/0263036 A1* | 10/2011 | Blauw et al. | 436/149 |
| 2012/0028429 A1* | 2/2012 | Batra et al. | 438/287 |

FOREIGN PATENT DOCUMENTS

DE    102011002854 A1    2/2012

OTHER PUBLICATIONS

Lundstrom et al., Catalytic Metals and Field Effect Devices—a Useful Combination, Sensors and Actuators, 81 (190), 15-20.*
International Search Report and Written Opinion corresponding to PCT Application No. PCT/US2013/076976, Mailed Apr. 2, 2013 (14 pages).
Ferain, I. et al., Metal Gate Thickness Optimization for MuGFET Performance Improvement, ESSDERC 2008, 38th European Solid-State Device Research Conference, Sep. 1, 2008, pp. 202-205 (4 pages).
Kim, Dai Hong et al., Gas Sensing Properties in Epitaxial SnO2 Films Grown in TiO2 Single Crystals with Various Orientations, Sensors and Actuators B: Chemical, vol. 147, No. 2, Jun. 3, 2010, pp. 653-659 (7 pages).

* cited by examiner

*Primary Examiner* — Asok K Sarkar
(74) *Attorney, Agent, or Firm* — Maginot Moore & Beck LLP

(57) ABSTRACT

A method of fabricating a semiconductor sensor device includes providing a substrate, supporting a source region and a drain region with the substrate, forming an insulator layer above the source region and the drain region, and forming a porous metallic gate region above the insulator layer using plasma enhanced atomic layer deposition (PEALD).

14 Claims, 3 Drawing Sheets

METHOD OF MANUFACTURING A SENSOR DEVICE HAVING A POROUS THIN-FILM METAL ELECTRODE

This application claims priority under 35 U.S.C. §119 to U.S. provisional application No. 61/745,573, filed on Dec. 22, 2012, the disclosure of which is incorporated herein by reference in its entirety.

FIELD

This disclosure relates generally to sensor devices and particularly to a method of manufacturing a gas sensor device having an electrode formed from a porous thin-film of metal.

BACKGROUND

One type of sensor device is a gas sensor device based on the field effect transduction principle. The gas sensor device includes a transducer having a source, a drain, and a gate electrode. A detection circuit is electrically connected to at least the source and the drain of the transducer. In response to the gate electrode being exposed to a target gas, the detection circuit detects an electrical change between the source and the drain that is related to the concentration of the target gas in the vicinity of the gate electrode.

Some gas sensor devices include a gate electrode formed from a layer of porous catalytic metal. The porous catalytic metal has more surface area compared to a solid or non-porous metal layer, such that there is a larger exposure area for the target gas to contact the catalytic material of the gate electrode. As a result, a sensor device having a porous gate electrode has an increased sensitivity level compared to a sensor device having a nonporous gate electrode.

The porous catalytic metal is typically applied to the sensor device in the form of a nanoparticle compound paste. Sometimes, the nanoparticle compound paste is difficult to control, resulting in variations in the thickness and the porosity of the catalytic metal layer. Also, the nanoparticle compound paste is typically applied in a layer that is thicker than desirable (i.e. greater than 1 µm). Furthermore, during a drying/sintering process, the nanoparticle compound paste sometimes cracks and becomes discontinuous.

Accordingly, further developments in forming a porous catalytic metal gate electrode for use as a gas-sensitive portion of a sensor device are desirable.

SUMMARY

According to an exemplary embodiment of the disclosure, a method of fabricating a semiconductor sensor device includes providing a substrate, supporting a source region and a drain region with the substrate, forming an insulator layer above the source region and the drain region, and forming a porous metallic gate region above the insulator layer using plasma enhanced atomic layer deposition (PEALD).

According to another exemplary embodiment of the disclosure, a semiconductor sensor device includes a plastic substrate, an insulator layer, and a porous metallic gate region. The plastic substrate is configured to support a source region and a drain region. The insulator layer is located above the substrate. The porous metallic gate region is located above the insulator layer.

BRIEF DESCRIPTION OF THE FIGURES

The above-described features and advantages, as well as others, should become more readily apparent to those of ordinary skill in the art by reference to the following detailed description and the accompanying figures in which.

DETAILED DESCRIPTION

Figure 1:
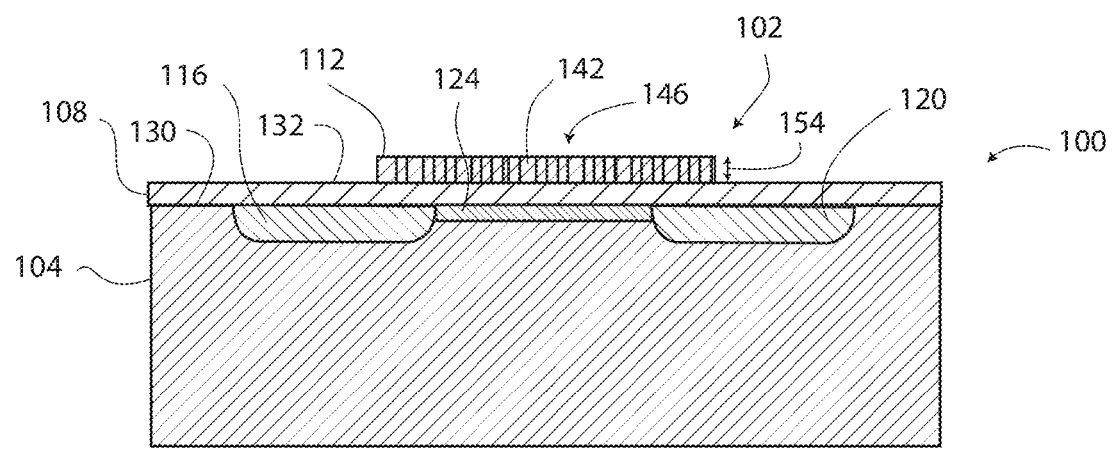
FIG. 1 is a cross sectional view of a semiconductor sensor device, as described herein, the sensor device includes a transducer having a source region, a drain region, and a gate electrode formed from a porous thin-film of metal.

For the purpose of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles of the disclosure as would normally occur to one skilled in the art to which this disclosure pertains.

With reference to FIG. 1, a semiconductor sensor device 100 includes a transducer 102 that is shown as a metal oxide semiconductor field effect transistor ("MOSFET"). In another embodiment, the transducer 102 is any other type of field effect transducer.

The transducer 102 includes a substrate 104, an insulator layer 108, and a gate electrode 112. The substrate 104 is configured to support a source region 116 and a drain region 120. The substrate 104, in one embodiment, is formed from silicon. In another embodiment, the substrate 104 is formed from any suitable material for supporting the source region 116 and the drain region 120. For example, in an exemplary embodiment, the substrate 104 is formed from plastic.

The source region 116 and the drain region 120 may be provided as doped regions formed in the substrate 104. The source region 116 is connected to an external detection circuit (not shown) and is configured to function as an electrical source of the sensor device 100. The drain region 120 is also connected to the external detection circuit and is configured to function as an electrical drain of the sensor device 100.

A channel region 124 is defined in the substrate 104 between the source region 116 and the drain region 120. In response to the sensor device 100 being exposed to a target gas, a conducting path is induced in the channel region 124, which enables a current flow between the source region 116 and the drain region 120. In at least one embodiment, the channel region 124 is passivated with the thermal oxide of the insulator layer 108 to provide the boundary conditions for forming the gate electrode 112.

The insulator layer 108, which is also referred to herein as an oxide layer or a seed layer, is located above the substrate 104. In the embodiment illustrated in FIG. 1, the insulator layer 108 is deposited on an upper surface 130 of the substrate 104 and is positioned between the gate electrode 112 and the source and drain regions 116, 120. The insulator layer 108, in at least one embodiment, is formed from silicon dioxide ($SiO_2$) that is either deposited or thermally grown. In another embodiment, the insulator layer 108 is formed from another type of suitable material, such as plastic. In yet another embodiment, the insulator layer 108 is a passivated portion of the substrate 104.

The gate electrode 112, which is also referred to herein as a porous metallic gate region, is located above the insulator layer 108. In the embodiment illustrated in FIG. 1, the gate electrode 112 is formed directly on an upper surface 132 of the insulator layer 108, such that the gate electrode is spaced apart from the source region 116, the drain region 120, and the channel region 124. The gate electrode 112 is a porous thin film of metal that includes a plurality of crystalline nanoparticles 142. The gate electrode 112 is formed from a catalytic metal, such as platinum, or any desired metal or metals. The gate electrode 112 defines a thickness 154.

Figure 2:
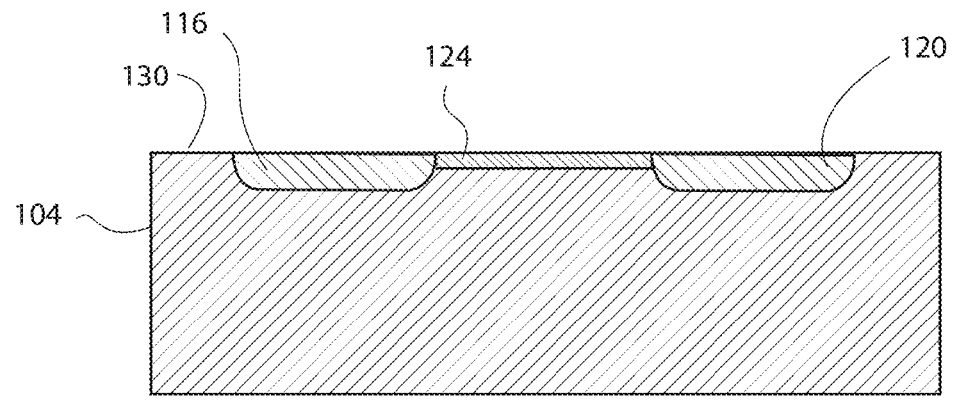
FIG. 2 is a cross sectional view similar to the cross sectional view of FIG. 1, showing a substrate having a source region and a drain region formed therein, and a channel region extending between the source region and the drain region.

With reference to FIG. 2, the sensor device 100 is fabricated, in one embodiment, according to the following process. First, the substrate 104 is provided. Second, the source region 116 and the drain region 120 are formed by way of diffusion, ion implementation, or any other suitable process.

Figure 3:
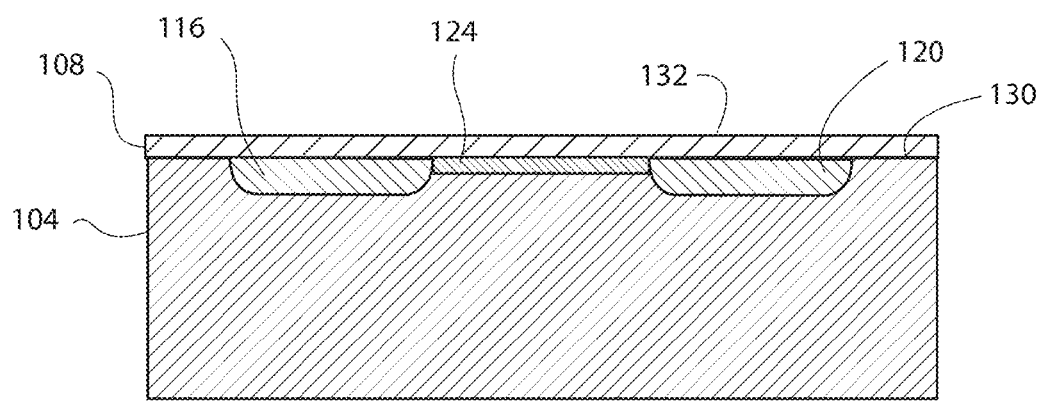
FIG. 3 is a cross sectional view similar to the cross sectional view of FIG. 1, showing an insulator layer formed on the substrate.

Next, as shown in FIG. 3, the insulator layer 108 is deposited onto the substrate 104 above the source region 116 and the drain region 120. Typically, a chemical vapor deposition process is used to form the insulator layer 108; however, any desired method may be used.

Referring again to FIG. 1, next the gate electrode 112 is formed on the oxide layer using a desired number of plasma enhanced atomic layer deposition (PEALD) cycles. Atomic layer deposition (ALD) is used to deposit materials by exposing a substrate (such as the insulator layer 108) to several different precursors sequentially. A typical deposition cycle begins by exposing the substrate to a precursor "A" which reacts with the substrate surface until saturation. This is referred to as a "self-terminating reaction." Next, the substrate is exposed to a precursor "B" which reacts with the surface until saturation. The second self-terminating reaction reactivates the surface. Reactivation allows the precursor "A" to react again with the surface. Typically, the precursors used in ALD include an organometallic precursor and an oxidizing agent such as water vapor or ozone.

An ALD cycle typically results, in an atomic layer being formed on the substrate. With each additional deposition cycle, another layer of deposited material may be formed on top of the previously formed layer. Accordingly, the final thickness of the deposited material is controlled by the number of cycles the substrate is exposed to, among other factors. Moreover, deposition using an ALD process is substantially unaffected by the orientation of the particular surface upon which material is to be deposited, such that an extremely uniform thickness of material may be realized both on the upper and lower horizontal surfaces and on the vertical surfaces. Additionally, depending on the interaction of the deposited material with the substrate, a nucleated film including a plurality of spaced apart nanoparticles (such as the nanoparticles 142) may be formed using ALD.

PEALD is a subset of ALD techniques that typically does not require exposure of the substrate to a high temperature, as is typically the done in thermally-driven ALD processes. Accordingly, PEALD is useable to forms films on substrates that would be destroyed or damaged in a thermally-driven ALD process. For example, in an embodiment in which the substrate is formed from silicon, the deposition temperature may be approximately two hundred seventy degrees Celsius. Whereas in an embodiment including a plastic substrate (or any other low melting temperature material), the deposition temperature may be approximately one hundred degrees Celsius. The lower deposition temperature of PEALD enables nanometer-thin controlled porous films (such as the gate electrode 112) to be formed on plastic substrates, flexible substrates, and other substrates, as are typically used in disposable sensors and lab-on-chip systems.

Figure 4:
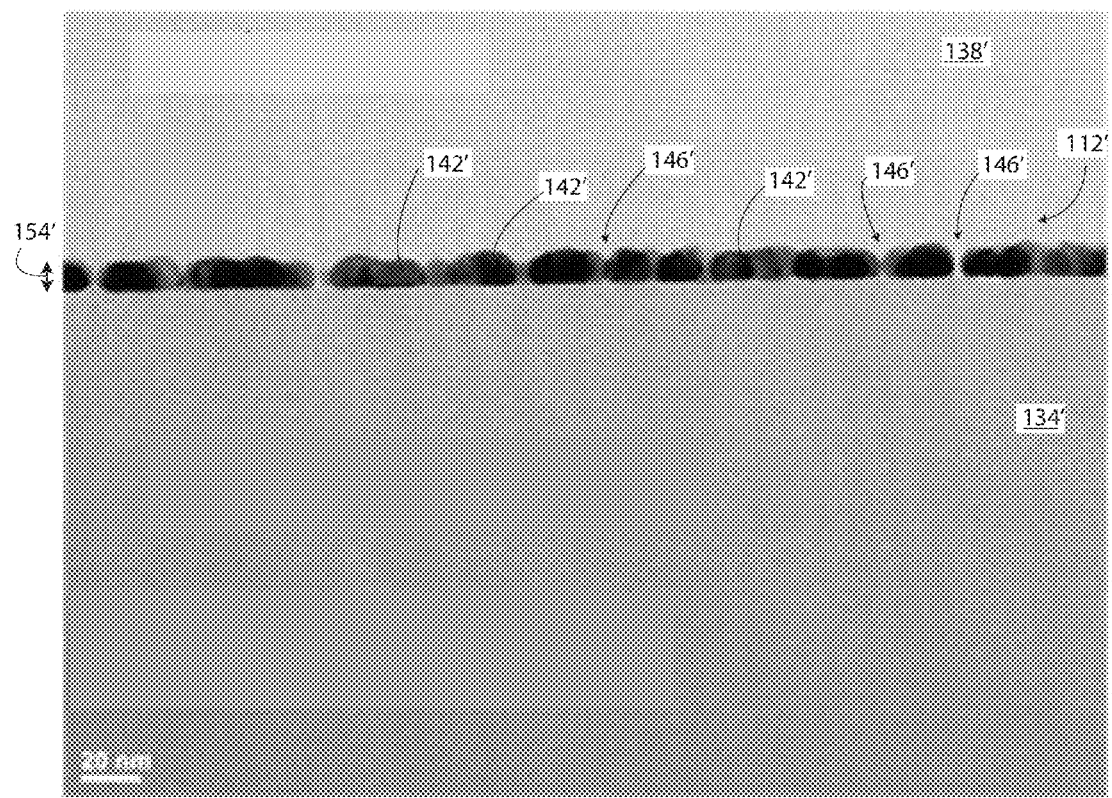
FIG. 4 is a transmission electron microscope view of a thin-film of platinum formed using approximately one hundred fifty cycles of plasma enhanced atomic layer deposition, the platinum film is positioned between a layer of silicon dioxide and a carbon cap and is an exemplary gate electrode of the semiconductor sensor device described herein.

With reference to FIG. 4, a microscopic view an exemplary gate electrode 112' formed using PEALD is provided to illustrate the nanoparticle structure of the gate electrode 112. In the illustrated embodiment, approximately one hundred fifty PEALD cycles were performed at a deposition temperature of approximately two hundred seventy degrees Celsius. The gate electrode 112' is formed on an insulator layer 108'. A carbon cap 138' is located on top of the gate electrode 112' and the insulator layer 108'. As illustrated, the gate electrode 112' defines a substantially uniform thickness 154'. The nanoparticles 142' are fused together and are configured define a plurality of spaces 146' therebetween. The spaces 146' make the thin-film gate electrode 112' porous and are configured to receive molecules of the target gas.

Figure 5:
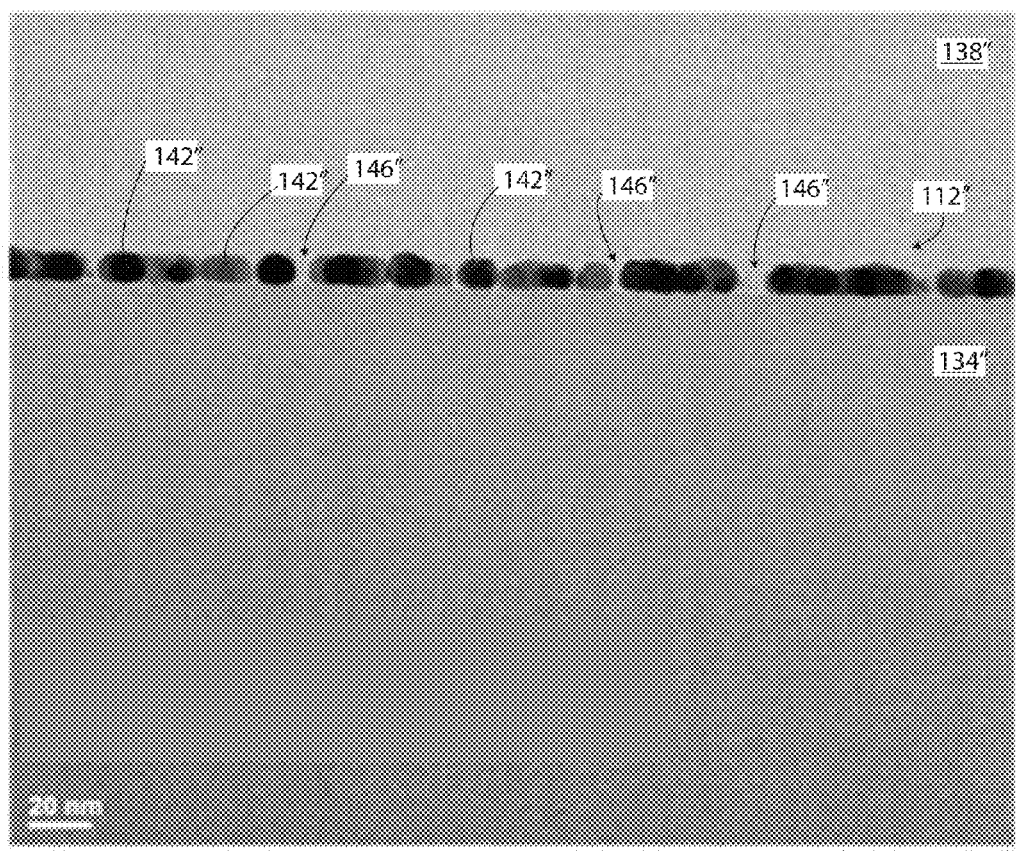
FIG. 5 is a transmission electron microscope view of a thin-film of platinum formed using approximately one hundred twenty five cycles of plasma enhanced atomic layer deposition, the platinum film is positioned between a layer of silicon dioxide and a carbon cap and is another exemplary gate electrode of the semiconductor sensor device described herein, a porosity of the platinum film of FIG. 5 is different than a porosity of the platinum film of FIG. 4.

As a comparison, in FIG. 5 another exemplary gate electrode 112" is shown that was formed using PEALD. The gate electrode 112" is formed on an insulator layer 108" of silicon dioxide and includes a carbon cap 138" positioned over the gate electrode 112". Approximately one hundred twenty five PEALD cycles were used to form the gate electrode 112". Accordingly the nanoparticles 142" of FIG. 5 are slightly smaller than the nanoparticles 142' of FIG. 4, which were formed with more PEALD cycles.

Based on the above, PEALD enables the gate electrode 112 to be formed with a desired thickness, nanoparticle size, and porosity. For example, forming the gate electrode 112 includes determining a desired magnitude of the thickness 154. Then, a desired number of PEALD cycles (i.e. a predetermined number of PEALD cycles) is determined based upon the desired magnitude of the thickness 154. Typically, an increase in the number of PEALD cycles results in a greater magnitude of the thickness 154, and a decrease in the number of PEALD cycles results in a lesser magnitude of the thickness. In one embodiment, at least one hundred cycles and not more than two hundred cycles of PEALD are used to form the gate electrode 112 to the desired magnitude of the thickness 154.

Forming the gate electrode 112 may also include determining a desired size of the nanoparticles 142. In particular, a desired number of PEALD cycles is determined based upon the desired size of the nanoparticles 142. Typically, an increase in the number of PEALD cycles results in larger nanoparticles 142, and a decrease in the number of PEALD cycles results in smaller nanoparticles. The "size" of the nanoparticles 142 may refer to the length, width, height, and/or any other dimension of the nanoparticles. For example, in FIG. 4, the size of the nanoparticles 142' is approximately 10 nm in the vertical dimension and approximately 10-30 nm in the horizontal dimension.

Additionally, forming the gate electrode 112 may also include determining a desired porosity of the gate electrode 112. After the desired porosity is determined, a desired number of PEALD cycles is determined based upon the desired porosity. Next, the desired number of PEALD cycles is performed to form the gate electrode 112. Typically, an increase in the number of PEALD cycles results in smaller spaces 146 (i.e. less porosity), and a decrease in the number of PEALD cycles results in larger spaces 146 (i.e. more porosity). The gate electrode 112' of FIG. 4 is less porous than the gate electrode 112" of FIG. 5 as a result of the increased number of PEALD cycles that were used to form the gate electrode 112'.

Depending on the embodiment, after formation of the gate electrode 112' a carbon cap 138', may be formed over the gate electrode, as shown in FIG. 4. The sensor device 100 is formable with or without the carbon cap 138' depending on the intended use of the sensor device and the composition of the target gas. The carbon cap 138' is configured to (i) adsorb the target gas, or (ii) enable the target gas to flow therethrough to the gate electrode 112'.

In operation, the sensor device 100 is configured to sense the presence of the target gas or target gasses in a space in which the sensor device is positioned. The gate electrode 112 is the active sensing area of the sensor device 100, and exposing the gate electrode 112 to the target gas causes an electrical change in the sensor device 100 that is detectable with the external detection circuit. Exemplary target gasses include carbon monoxide, nitrogen dioxide ($NO_2$), ammonia ($NH_3$), methane ($CH_4$), volatile organic compounds (VOCs), and the like.

Due at least to the small size of the sensor device 100, it is usable to detect gasses in a variety of applications such as automobile exhaust systems, home appliances, laptops, handheld or portable computers, mobile telephones, smart phones, wireless devices, tablets, personal data assistants (PDAs), portable music players, film cameras, digital cameras, GPS receivers and other satellite navigation systems, electronic reading displays, projectors, cockpit controls, game consoles, earpieces, headsets, hearing aids, wearable display devices, security systems, and other applications as desired by those ordinary skill in the art.

In another embodiment of the sensor device 100, the gate electrode 112 is formed on a gate electrode assembly (not shown), which includes an oxide layer instead of being formed directly on the oxide layer 108. In any embodiment, the gate electrode 112 is either floating or connected.

Other metals besides platinum are usable with PEALD to form a nanometer thin porous film, as may be useful for detecting a particular target gas or gasses. Also, the porous layer of metal nanoparticles 142 may be formed on a seed layer 108 other than silicon dioxide, in other embodiments. The feasibility of other seeding materials depends on the chemical processes involved during a seeding stage of the PEALD process.

The PEALD approach of forming the gate electrode 112, as described above, is also useful for forming other types of sensors including, but not limited to, humidity sensors, biosensors, and chemical reaction chambers.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A method of fabricating a semiconductor sensor device comprising:
    providing a substrate;
    supporting a source region and a drain region with the substrate;
    forming an insulator layer above the source region and the drain region; and
    forming a porous metallic gate region above the insulator layer using plasma enhanced atomic layer deposition (PEALD).

2. The method of claim 1, wherein forming the porous metallic gate region comprises:
    determining a desired porous metallic gate region thickness;
    determining a desired number of PEALD cycles based upon the determined desired porous metallic gate region thickness; and
    performing the determined desired number of PEALD cycles.

3. The method of claim 2, wherein the determined desired number of PEALD cycles is at least one hundred cycles and not more than two hundred cycles.

4. The method of claim 1, wherein forming the porous metallic gate region comprises:
    determining a desired porous metallic gate region nanoparticle size;
    determining a desired number of PEALD cycles based upon the determined desired porous metallic gate region nanoparticle size; and
    performing the determined desired number of PEALD cycles.

5. The method of claim 1, wherein forming the porous metallic gate region comprises:
    determining a desired porous metallic gate region porosity;
    determining a desired number of PEALD cycles based upon the determined desired porous metallic gate region porosity; and
    performing the determined desired number of PEALD cycles.

6. The method of claim 1, wherein:
    forming the insulator layer comprises depositing a silicon dioxide layer on an upper surface of the substrate.

7. The method of claim 6, wherein:
    providing the substrate comprises providing a plastic substrate.

8. The method of claim 7, wherein forming a porous metallic gate region comprises:
    forming a porous catalytic metal gate region.

9. The method of claim 8, wherein forming a porous catalytic metal gate region comprises:
    forming a porous platinum gate region on an upper surface of the silicon dioxide layer.

10. A semiconductor sensor device comprising:
    a plastic substrate configured to support a source region and a drain region;
    an insulator layer located above the substrate; and
    a porous metallic gate region located above the insulator layer and including a plurality of nanoparticles formed using a predetermined number of cycles of plasma enhanced atomic layer deposition.

11. The semiconductor sensor device of claim 10, wherein:
    the insulator layer includes a silicon dioxide layer deposited on an upper surface of the substrate.

12. The semiconductor sensor device of claim 11, wherein the porous metallic gate region includes a catalytic metal.

13. The semiconductor sensor device of claim 12, wherein:
    the porous metallic gate region is formed on an upper surface of the silicon dioxide layer, and
    the catalytic metal includes platinum.

14. The semiconductor sensor device of claim 10, wherein:
    a plurality of spaces is defined between the plurality of nanoparticles, and
    the plurality of spaces is configured to receive molecules of a target gas.

* * * * *